(12) United States Patent
Dorok et al.

(10) Patent No.: US 10,403,824 B2
(45) Date of Patent: Sep. 3, 2019

(54) ELECTRONIC DEVICE AND COMPOUND

(71) Applicant: Novaled GmbH, Dresden (DE)

(72) Inventors: Sascha Dorok, Dresden (DE); Ina Steudtner, Dresden (DE); Ulrich Heggemann, Dresden (DE); Steffen Runge, Leipzig (DE); Manuela Klose, Dresden Langebrueck (DE)

(73) Assignee: Novaled GmbH, Dresden (DE)

( * ) Notice: Subject to any disclaimer, the term of this patent is extended or adjusted under 35 U.S.C. 154(b) by 0 days.

(21) Appl. No.: 15/323,905

(22) PCT Filed: Jul. 3, 2015

(86) PCT No.: PCT/EP2015/065245
§ 371 (c)(1),
(2) Date: Jan. 4, 2017

(87) PCT Pub. No.: WO2016/001425
PCT Pub. Date: Jan. 7, 2016

(65) Prior Publication Data
US 2017/0155047 A1 Jun. 1, 2017

(30) Foreign Application Priority Data
Jul. 4, 2014 (EP) .................................... 14175863

(51) Int. Cl.
*H01L 51/00* (2006.01)
*C07D 235/30* (2006.01)
(Continued)

(52) U.S. Cl.
CPC .......... *H01L 51/005* (2013.01); *C07C 211/53* (2013.01); *C07C 279/18* (2013.01);
(Continued)

(58) Field of Classification Search
CPC ... C07C 211/53; C07C 279/18; C07D 233/50; C07D 235/30; C07D 295/125;
(Continued)

(56) References Cited

U.S. PATENT DOCUMENTS 3,916,068 A 10/1975 Kohmura et al.
4,864,075 A * 9/1989 Thompson ........... B01D 17/047
210/705
(Continued)

FOREIGN PATENT DOCUMENTS

DE 1170931 B 5/1964
EP 1723946 A1 11/2006
(Continued)

OTHER PUBLICATIONS

Yueqi Mo et al., "Ultraviolet Emitting conjugated polymer based on poly(9,9'-alkyl-3,6-silafluorene) with wide band-gap 4.0eV", Supplementary Material (ESI) for Chemical Communications, The Royal Society of Chemistry, 2005, 1-15. (Year: 2005).*
Quaternary Carbon, Wikipedia, Dec. 2, 2017. (Year: 2017).*
PCT International Search Report and Written Opinion for PCT Application No. PCT/EP2015/065245 dated May 6, 2016.
Belding et al., "Synthesis and Theoretical Investigation of a 1,8-Bis(bis(diisopropylamino)cyclopropeniminyl)naphthalene Proton Sponge Derivative," Chem. Eur. J., 2014, 20:1032-1037.
Garnier et al., "Structure and Reactivity in Neutral Organic Electron Donors Derives from 4-Dimthylaminopyridine," Beilstein J. Org. Chem., 2010, 6(73):1-8.
Peters et al., "Tuning the Properties of Redox-Active Guanidino-Functionalized Aromatic Ligands by Substitution: Experiment and Theory," Eur. J. Inorg. Chem., 2012, 1620-1631.
(Continued)

*Primary Examiner* — Douglas J McGinty
(74) *Attorney, Agent, or Firm* — Eversheds Sutherland (US) LLP

(57) ABSTRACT

The invention relates to an electronic device comprising a compound having Formula (1): $AB_x$ (1), wherein A is a structural moiety that consists of at least two atoms and comprises a conjugated system of delocalized electrons, each B is independently selected from an imine functional group (1a), wherein $R^1$, $R^2$, $R^3$, $R^4$ are independently selected from $C_1$-$C_{30}$ alkyl, $C_2$-$C_{30}$ alkenyl, $C_2$-$C_3$ alkinyl, $C_3$-$C_{30}$ cycloalkyl, $C_6$-$C_{30}$ aryl, $C_2$-$C_{30}$ heteroaryl, $C_7$-$C_{30}$ arylalkyl, $C_3$-$C_{30}$ heteroarylalkyl, the wave line represents a covalent bond to the imine nitrogen atom, G is in each group (1a) independently selected from a quarternary carbon atom and from a cyclopropenylidene structural moiety, x is an integer equal one or higher, preferably equal two or higher, and the lone electron pair of the imine nitrogen atom and/or the pi-electrons of the imine double bond of at least one group B is conjugated with the conjugated system of delocalized electrons comprised in the structural moiety A, with the proviso that two or more of the substituents $R^1$, $R^2$, $R^3$, $R^4$ may be connected to form a ring that may contain also unsaturation and, if any of the substituents $R^1$, $R^2$, $R^3$, $R^4$ comprises two or more carbon atoms, up to one third of the overall count of the carbon atoms in the substituent or in any ring formed by two connected substituents can be replaced with heteroatoms independently selected from O, S, N and B as well as to an electrically semiconducting material and a compound for use in the electronic device.

(Ia)

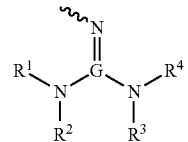

20 Claims, 2 Drawing Sheets

(51) Int. Cl.

| | |
|---|---|
| *C07D 295/125* | (2006.01) |
| *C07C 279/18* | (2006.01) |
| *C08G 73/02* | (2006.01) |
| *C07C 211/53* | (2006.01) |
| *C07D 233/50* | (2006.01) |
| *C07D 295/13* | (2006.01) |
| *H01L 51/42* | (2006.01) |
| *H01L 51/44* | (2006.01) |

(52) U.S. Cl.
CPC ......... *C07D 233/50* (2013.01); *C07D 235/30* (2013.01); *C07D 295/125* (2013.01); *C07D 295/13* (2013.01); *C08G 73/02* (2013.01); *C08G 73/026* (2013.01); *H01L 51/002* (2013.01); *H01L 51/0061* (2013.01); *H01L 51/0067* (2013.01); *H01L 51/0069* (2013.01); *H01L 51/0072* (2013.01); *H01L 51/4253* (2013.01); *H01L 51/441* (2013.01); *C07C 2601/02* (2017.05); *H01L 51/0046* (2013.01); *H01L 51/424* (2013.01); *Y02E 10/549* (2013.01)

(58) Field of Classification Search
CPC .... C07D 295/13; C08G 73/02; C08G 73/026; H01L 51/002; H01L 51/005; H01L 51/0061; H01L 51/0067; H01L 51/0069; H01L 51/0072; H01L 51/4253; H01L 51/441
USPC .................................. 252/500; 429/188, 189
See application file for complete search history.

(56) References Cited

U.S. PATENT DOCUMENTS

| | | | | |
|---|---|---|---|---|
| 5,214,208 | A * | 5/1993 | Tanaka | G03G 9/09775 430/108.21 |
| 6,902,850 | B2 * | 6/2005 | Wariishi | H01B 1/122 429/188 |
| 6,911,595 | B2 * | 6/2005 | Yoshikawa | C07D 213/76 136/256 |
| 10,003,024 | B2 * | 6/2018 | Pan | C08G 61/12 |
| 10,205,207 | B2 * | 2/2019 | Wijaya | H01M 4/133 |
| 2006/0269498 | A1 | 11/2006 | Malle et al. | |
| 2008/0269525 | A1 | 10/2008 | Bertrand et al. | |
| 2012/0119191 | A1 * | 5/2012 | Dorok | C07F 9/65583 257/40 |
| 2012/0223296 | A1 * | 9/2012 | Werner | H01L 51/006 257/40 |
| 2012/0295148 | A1 * | 11/2012 | Yoshimura | H01M 2/1653 429/144 |
| 2018/0301288 | A1 * | 10/2018 | Irwin | H01G 9/2018 |

FOREIGN PATENT DOCUMENTS

| | | |
|---|---|---|
| GB | 1050978 | 12/1966 |
| WO | 01/44311 A1 | 6/2001 |
| WO | 2013/059118 A1 | 4/2013 |

OTHER PUBLICATIONS

Vitske et al., "Synthesis of the First Coordination Compounds of the New Strong Molecular Electron Donor and Double Proton Sponge 1,4,5,8-Tetrakis(tetramethylguanidino)naphthalene," Eur. J. Inorg. Chem., 2010, 115-126.

Chinese Office Action for CN Application No. 201580042286.2 dated Aug. 3, 2018 (51 pages with English translation).

* cited by examiner

| |
|---|
| 38 |
| 37 |
| 36 |
| 35 |
| 34 |
| 33 |
| 32 |
| 31 |
| 30 |

ELECTRONIC DEVICE AND COMPOUND

CROSS REFERENCE TO RELATED APPLICATIONS

This application is a U.S. national stage application of PCT/EP2015/065245, filed Jul. 3, 2015, which claims priority to European Application No. 14175863.1, filed Jul. 4, 2014. The contents of these applications are hereby incorporated by reference.

The invention relates to an electronic device, electrically doped semiconducting material and a compound for use in the electronic device.

BACKGROUND OF THE INVENTION

Among organic electronic devices, organic solar cells (OSCs), also known as organic photovoltaic (OPV) devices, have the most variable device architectures. Typically, they comprise at least one organic semiconducting layer that is arranged between two electrodes.

The organic layer can be a blend of a donor and an acceptor such as P3HT (poly3-hexyl-tiophene) and PCBM (phenyl C61 Butyric Acid Methyl Ester). Such simple device structures only achieve reasonably efficiencies if interfacial injection layers are used to facilitate charge carrier injection/extraction (Liao et al., Appl. Phys. Lett., 2008.92: p. 173303). Other organic solar cells have multilayer structures, sometimes even hybrid polymer/small molecule structures. Also tandem or multi-unit stacks are known (see US 2007/090371 A1, or Ameri, et al., Energy & Env. Science, 2009.2: p. 347). Multi-layer devices can be easier optimized since different layers can comprise different compounds and their mixtures which are suitable for different functions. Typical functional layers are transport layers, photoactive layers, injection layers, etc.

In OPV, under optically active compounds are understood compounds with a high absorption coefficient, for at least a certain wavelength range of the solar spectra, which compounds convert absorbed photons into excitons. Excitons may dissociate in free charges which may be finally extracted as photocurrent. The photoactive compounds are typically used in a donor-acceptor heterojunction, where at least one of the donor or the acceptor is the light absorbing compound. The interface of the donor-acceptor heterojunction is responsible for separating the generated excitons into charge carriers. The heterojunction can be a bulk-heterojunction (a blend), or a flat (also called planar) heterojunction, additional layers can also be provided (Hong et al, J. Appl. Phys., 2009.106: p. 064511).

The exciton loss by recombination is to be minimized for high efficiency OPV devices. Therefore, the compounds in the heterojunction must have high charge carrier mobilities and high exciton diffusion lengths. The excitons have to be separated into charge carriers at the heterointerface and the charge carriers have to leave the optically active region before any recombination takes place. For that reasons, currently, fullerenes ($C_{60}$, $C_{70}$, PCBM, and so on) are the preferred choice as acceptor materials in OPV devices.

Charge transport materials for opto-electronic devices are required to be transparent, at least in the wavelengths wherein the device is active, and have good semiconducting properties. These semiconducting properties are intrinsic, such as energy levels or mobility, or extrinsic, such as charge carrier density. The charge carrier density can also be extrinsically influenced by doping the compound with an electrical redox dopant.

OSCs very often require the use of at least one n-dopant in a n-doped electron transport layer, or as a pure interlayer promoting electron injection from a conductive layer into a semiconductor or from a semiconductor into another semiconductor.

Various strong redox n-dopants are known, such as tetrakis(1,3,4,6,7,8-hexahydro-2H-pyrimido [1,2-a]pyrimidinato)ditungsten (II) from EP 1 768 200 B1, bis(2,2'-terpyridin)ruthenium, and others. One main problem of strongly reducing n-dopants is that since they are strong electron donors, they easily degrade by reacting with atmospheric oxygen. There are not many known compounds which are able to directly work as n-dopants which are also air stable. Precursor-compounds were developed with the aim to provide air stable organic compounds and being able to work as n-dopants, examples of such precursors are disclosed in WO 2007/107306 A1.

For low LUMO compounds used in OSCs, such as fullerenes (e.g. $C_{60}$) or fullerene derivatives (e.g. PCBM), phosphine imine compounds comprising a conjugated system of delocalized electrons were demonstrated in WO2012/175219 as sufficiently strong n-dopants, being still air stable. Nevertheless, broader offer of air stable and sufficiently strong n-dopants for organic electronics, allowing a selection of an appropriate dopant for various device designs and simplification and high reproducibility of manufacturing procedures, particularly in mass production, does still represent an unmet demand.

SUMMARY OF THE INVENTION

It is the object of the invention to provide alternative devices with good performance and smooth and reproducible processability. Another object of the invention is to provide alternative air stable semiconducting materials and compounds for such materials.

The object is achieved by the electronic device comprising a compound having Formula 1

$$AB_x \quad (1),$$

wherein
A is a structural moiety that consists of at least two atoms and comprises a conjugated system of delocalized electrons,
each B is independently selected from an imine functional group (Ia)

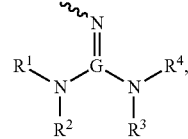

(Ia)

wherein $R^1$, $R^2$, $R^3$, $R^4$ are independently selected from $C_1$-$C_{30}$ alkyl, $C_2$-$C_{30}$ alkenyl, $C_2$-$C_{30}$ alkinyl, $C_3$-$C_{30}$ cycloalkyl, $C_6$-$C_{30}$ aryl, $C_2$-$C_{30}$ heteroaryl, $C_7$-$C_{30}$ arylalkyl, $C_3$-$C_{30}$ heteroarylalkyl,
the wave line represents a covalent bond to the imine nitrogen atom,
G is in each group (Ia) independently selected from a quarternary carbon atom and from a cyclopropenylidene structural moiety,
x is an integer equal one or higher, preferably equal two or higher, and the lone electron pair of the imine nitrogen atom and/or the pi-electrons of the imine double bond of at least one group B is conjugated with the conjugated system of delocalized electrons comprised in the structural moiety A, with the proviso that two or more of the substituents $R^1$, $R^2$, $R^3$, $R^4$ may be connected to form a ring that may contain also unsaturation and, if any of the substituents $R^1$, $R^2$, $R^3$, $R^4$ comprises two or more carbon atoms, up to one third of the overall count of the carbon atoms in the substituent or in any ring formed by two connected substituents can be replaced with heteroatoms independently selected from O, S, N and B.

Preferably, x is equal two or higher; more preferably, x is an integer selected from 2, 3 and 4. Also preferably, the lone electron pairs of the imine nitrogen atoms and/or the pi-electrons of the imine double bonds of at least two groups B are conjugated with the conjugated system of delocalized electrons comprised in the structural moiety A. More preferably, the lone electron pairs of the imine nitrogen atoms and/or the pi-electrons of the imine double bonds of all groups B are conjugated with the conjugated system of delocalized electrons comprised in the structural moiety A.

Even more preferably, A is a $C_3$-$C_{40}$ arene or $C_2$-$C_{40}$ heteroarene structural moiety that contains one conjugated system of delocalized electrons.

Most preferably, A is a $C_6$-$C_{18}$ arene or $C_4$-$C_{18}$ heteroarene structural moiety and the lone electron pairs of the imine nitrogen atoms and/or the pi-electrons of the imine double bonds of all groups B are conjugated with the conjugated system of delocalized electrons comprised in the structural moiety A.

In a preferred embodiment, the electronic device is an organic electronic device.

According to a preferred embodiment of the invention, the compound according to Formula 1 is used as a n-dopant.

According to a preferred embodiment, the electronic device has a layered structure comprising several layers, wherein at least one of the layers comprises the compound of Formula 1. The electronic device may further comprise an electron transport layer. Alternatively or supplementary, the electronic device may comprise a first electrode and/or a second electrode.

In a preferred embodiment, the layer of the electronic device comprising the compound of Formula 1 is an electron transport layer. More preferably, the electronic device comprises an electron transport layer which comprises an electron transport compound and the compound according to Formula 1 forming a homogeneous mixture. According to another preferred mode of the invention, the layer of the electronic device comprising the compound of Formula 1 is in direct contact to an electron transport layer. In a preferred mode of the invention, the electron transport layer comprises a fullerene or a fullerene derivative as its main component.

If the compound of Formula 1 is used neat as an electron injecting and/or extracting layer, the layer of the electronic device comprising the compound of Formula 1 has preferably a thickness of less than 5 nm.

Preferably, the layer of the electronic device comprising the compound of Formula 1 is in direct contact to an electrode, more preferably a cathode. In addition or alternatively, the layer comprising the compound according to Formula 1 is arranged between the electron transport layer and the cathode.

In one aspect of the invention, the electronic device comprises a connecting unit (which is alternatively called also pn-junction or charge generating layer). Connecting units serve in tandem devices, e.g. in tandem OLEDs or in tandem solar cells, for electrical connection of particular devices forming the tandem device. In a preferred embodiment, the layer of the electronic device comprising the compound of Formula 1 is part of the connecting unit.

In a preferred mode of the invention, the electronic device is a solar cell, preferably an organic solar cell (OSC). The solar cell can comprise, for example, an anode, a cathode and a light absorbing layer. In a preferred embodiment, the organic solar cell further comprises the compound according to Formula 1, wherein the compound is comprised between the light absorbing layer and the cathode. In a preferred aspect of the invention, the organic solar cell comprises a pi, ni, or pin structure, comprising a first p, i, or n layer each. Here, p denotes a p-doped hole transport layer, n denotes a n-doped electron transport layer, and i is an intrinsic photoactive layer (see US 2007/090371 A1 for further details). The transport layers have a greater HOMO-LUMO gap than the photoactive layer (HOMO—highest occupied molecular orbital, LUMO—lowest unoccupied molecular orbital).

The solar cell can preferentially comprise a light absorbing unit comprising the light absorbing layer and an additional light absorbing unit comprising an additional light absorbing layer. The connecting unit can be a pn-junction connecting the light absorbing unit to the additional light absorbing unit. Preferably, the connecting unit is a pn-junction connecting the light absorbing unit to the additional light absorbing unit in a tandem device or in a multiple stacked device. Multiple stacked devices are devices with three or more light absorbing units, sometimes also called multi tandem. Multiple stacked pin, pi, or ni devices are preferred. In addition or in alternative, the connecting unit can be a pn-junction connecting the cathode or the anode to the light absorbing unit.

Further object is achieved by electrically doped semiconducting material comprising at least one electron transport matrix compound and at least one n-dopant having Formula 1

$$AB_x \tag{1},$$

wherein

A is a structural moiety that consists of at least two atoms and comprises a conjugated system of delocalized electrons, each B is independently selected from an imine functional group (Ia)

wherein $R^1$, $R^2$, $R^3$, $R^4$ are independently selected from $C_1$-$C_{30}$ alkyl, $C_2$-$C_{30}$ alkenyl, $C_2$-$C_{30}$ alkinyl, $C_3$-$C_{30}$ cycloalkyl, $C_6$-$C_{30}$ aryl, $C_2$-$C_{30}$ heteroaryl, $C_7$-$C_{30}$ arylalkyl, $C_3$-$C_{30}$ heteroarylalkyl, with the proviso that two or more of the substituents $R^1$, $R^2$, $R^3$, $R^4$ may be connected to form a ring that may contain also unsaturation and, if any of the substituents $R^1$, $R^2$, $R^3$, $R^4$ comprises two or more carbon atoms, up to one third of the overall count of the carbon atoms in the substituent or in any ring formed by two connected substituents can be replaced with heteroatoms selected from O, S, N and B, the wave line represents a covalent bond to the imine nitrogen atom, G is in each group (Ia) independently selected from a quarternary carbon atom and from a cyclopropenylidene structural moiety, and x is an integer equal one or higher, and the lone electron pair of the imine nitrogen atom and/or the pi-electrons of the imine double bond of at least one group B is conjugated with the conjugated system of delocalized electrons comprised in the structural moiety A.

The redox pair consisting of equimolar amounts of the matrix compound and its anion radical can have the value of its redox potential measured by cyclic voltammetry under the same conditions as for a comparative redox pair equal or higher than the comparative redox couple consisting of equimolar amounts of tetracyanoquinodimethane and its anion radical, however, it is preferred that the redox potential of each compound comprised in the matrix material is more negative than the redox potential of the comparative redox couple TCNQ/TCNQ anion radical.

Further, the term "more negative" will be simplified as "lower". More preferably, the redox potential of the matrix material is lower than −0.50 V versus standard redox couple ferrocenium/ferrocene (Fc$^+$/Fc), even more preferably, lower than −0.65 V vs. Fc$^+$/Fc, even more preferably lower than −0.80 V vs. Fc$^+$/Fc, most preferably lower than −0.90 V vs. Fc$^+$/Fc.

Third object of the invention is achieved by compound having Formula 1

wherein

A is a structural moiety that consists of at least two atoms and contains one conjugated system of delocalized electrons, each B is independently selected from an imine functional group (Ia)

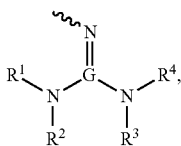

wherein $R^1$, $R^2$, $R^3$, $R^4$ are independently selected from $C_1$-$C_{30}$ alkyl, $C_2$-$C_{30}$ alkenyl, $C_2$-$C_{30}$ alkinyl, $C_3$-$C_{30}$ cycloalkyl, $C_6$-$C_{30}$ aryl, $C_2$-$C_{30}$ heteroaryl, $C_7$-$C_{30}$ arylalkyl, $C_3$-$C_{30}$ heteroaryl alkyl, the wave line represents a covalent bond to the imine nitrogen atom, G is in each group (Ia) independently selected from a quarternary carbon atom and from a cyclopropenylidene structural moiety, x is an integer equal two or higher, and the lone electron pair of the imine nitrogen atom and/or the pi-electrons of the imine double bond of each group B is conjugated with the conjugated system of delocalized electrons comprised in the structural moiety A, with the proviso that if G is the quaternary carbon atom, or if preferably G is the quaternary carbon atom or the cyclopropenylidene structural moiety, at least one of $R^1$, $R^2$ and at least one of $R^3$, $R^4$ is independently selected from the group consisting of $C_6$-$C_{30}$ aryl and $C_2$-$C_{30}$ heteroaryl, or $R^1$ is connected to $R^2$ and $R^3$ is connected to $R^4$ to form a ring that may contain also unsaturation, and if any of the substituents $R^1$, $R^2$, $R^3$, $R^4$ comprises two or more carbon atoms, up to one third of the overall count of the carbon atoms in the substituent or in any ring formed by two connected substituents can be replaced with heteroatoms selected from O, S, N and B.

Preferably, the structural moiety A is selected from the group consisting of $C_3$-$C_{40}$ arene and $C_2$-$C_{40}$ heteroarene, more preferably from the group consisting of $C_6$-$C_{18}$ arene and $C_4$-$C_{61}$ heteroarene.

DETAILED DESCRIPTION OF THE INVENTION

The invention has the advantages that high conductivity can be achieved by doping typical electron transport matrices (ETMs) used for OSCs. With the use of the compound according to Formula 1, it is possible to obtain, depending on the matrix, conductivities in the desirable range $10^{-2}$-$10^{-6}$ S/cm, provided dopant concentrations about 10 mol. %, as most frequently used in organic semiconductors. Furthermore, the compound according to Formula 1 has a high stability allowing it to be processed, for example, in vacuum, e.g. by vacuum thermal evaporation (VTE), or by organic vapor phase deposition (OVPD). Alternatively, the compound according to Formula 1 can be deposited by solution processing under inert atmosphere or even exposed to air.

In a preferred embodiment, the compound according to Formula 1 is inserted in a matrix material forming a doped layer. Herewith, cation radicals derived from the molecules of the compound according to Formula 1 are formed, in particular by the transfer of at least one electron from the compound according to Formula 1 to the surrounding matrix material. In the electron transfer process, anion radicals of the matrix material are also formed. In this way, the matrix material obtains an electron conductivity which is increased in comparison to the conductivity of the undoped matrix material.

The matrix material may consist of one or more matrix compounds. The conductivity of an electrically undoped matrix material is generally approximately $10^{-8}$ S/cm or less, in particular often around $10^{-10}$ S/cm. The matrix material should have a sufficiently high purity. Such purity can be achieved using conventional methods, for example gradient sublimation. By doping, the conductivity of the doped semiconducting material can be increased to more than $10^{-6}$ S/cm. Matrix compounds used in OLEDs have their redox potential (expressed according to IUPAC convention as the potential of the redox pair consisting of the electrically neutral matrix molecule and of its anion radical) preferably in the range between −2.0 and −3.0 V vs. Fc/Fc$^+$. In OSCs, compounds applicable as electron transport matrix have redox potential of less than −0.3 V vs. Fc/Fc$^+$, preferably less than −0.8 V vs. Fc/Fc$^+$. The notation Fc/Fc$^+$ relates to the redox pair ferrocene/ferrocenium, which is used throughout this application as reference redox potential equal zero, because the Fc/Fc$^+$ couple is most frequently used as standard reference redox pair in electrochemical potential determinations, for example by cyclic voltammetry (CV). Details of cyclovoltammetry and other methods to determine reduction potentials and the relation of the ferrocene/ferrocenium reference couple to various reference electrodes can be found in A. J. Bard et al., "Electrochemical Methods: Fundamentals and Applications", Wiley, 2. Edition, 2000.

In the present application, a dopant is to be understood as a compound which is mixed in a matrix material ("the matrix material is doped with the dopant"). It is also common in the state of the art to use the term "electrical dopant", or just "n-dopant" for the dopant for an ETM.

The layer of the electronic device comprising the compound of Formula 1 arranged adjacent to the electron transport layer can be used in an OSC as an electron extracting layer. It was found that the compound according to Formula 1 can be used as an electron injection layer in an electronic component, preferably between an electrode and a semiconductor layer which may be doped. Alternatively or supplementary, the compound according to Formula 1 can be used as a blocking layer, preferably between an absorbing layer and a transport layer, or as a semiconductor layer in electronic components.

In one preferred aspect of the invention, all organic layers of the electronic device are constituted from small molecules. Preferentially, the small molecules can be deposited by VTE (vacuum thermal evaporation).

In another aspect of the invention, at least one organic semiconducting layer comprises a polymer, wherein the polymer layer and/or at least one additional semiconducting layer comprise a compound according to Formula 1.

The compounds according to Formula 1 have a special advantage of forming very stable n-doped layers with a relatively high conductivity.

If the compound of Formula 1 is used in a solar cell in a mixture with at least one electron transport matrix compound in an electron transport layer, it is advantageous that the electron transport layer has a thickness more than 5 nm, preferably more than 10 nm, more preferably more than 30 nm, even more preferably more than 50 nm, particularly if used with an ITO anode that has often high roughness. If the ETL comprising the compound of Formula 1 is used adjacent to a rough cathode, e.g. to an ITO cathode, without a smoothing interlayer between the rough cathode and the ETL, it can be advantageous to use an ETL as thick as 100 nm, 150 nm, or even thicker.

As many electron transport matrix compounds used in OSCs, e.g. fullerenes and their derivatives, have significant optical absorbance which is favourable for their use in absorption layers but undesired for their use in transport layers, it is very advantageous that the inventive compounds have lower optical absorbance in comparison with such matrix compounds and that they can be used in the n-doped electron transport semiconducting materials in high concentrations, what mitigates the undesired, parasitic optical absorption in the ETL. For application in thick ETLs, particularly in ETL thicker than 50 nm and especially in ETLs thicker than 100 nm, it is advantageous to that the compound of Formula 1 is used in a concentration higher than 10 wt. %, more preferably higher than 20 wt. %, and even more preferably as high as 30 wt. % or higher.

DESCRIPTION OF EXEMPLARY EMBODIMENTS

In the following, exemplary embodiments are disclosed with reference to figures of a drawing.

The figures show:

Figure 1:
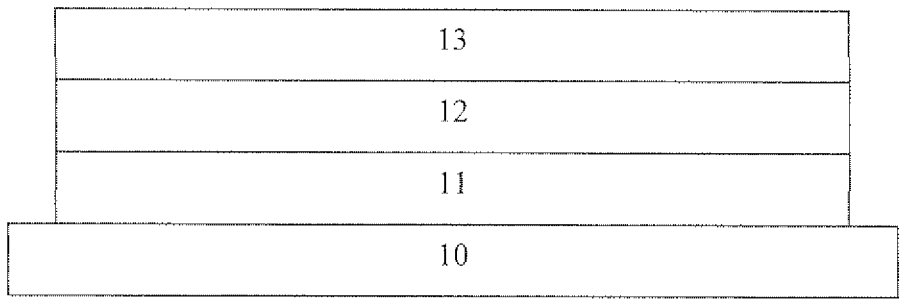
FIG. 1 is a schematic diagram representing a stack of layers which forms a solar cell.
Figures 3, 4:
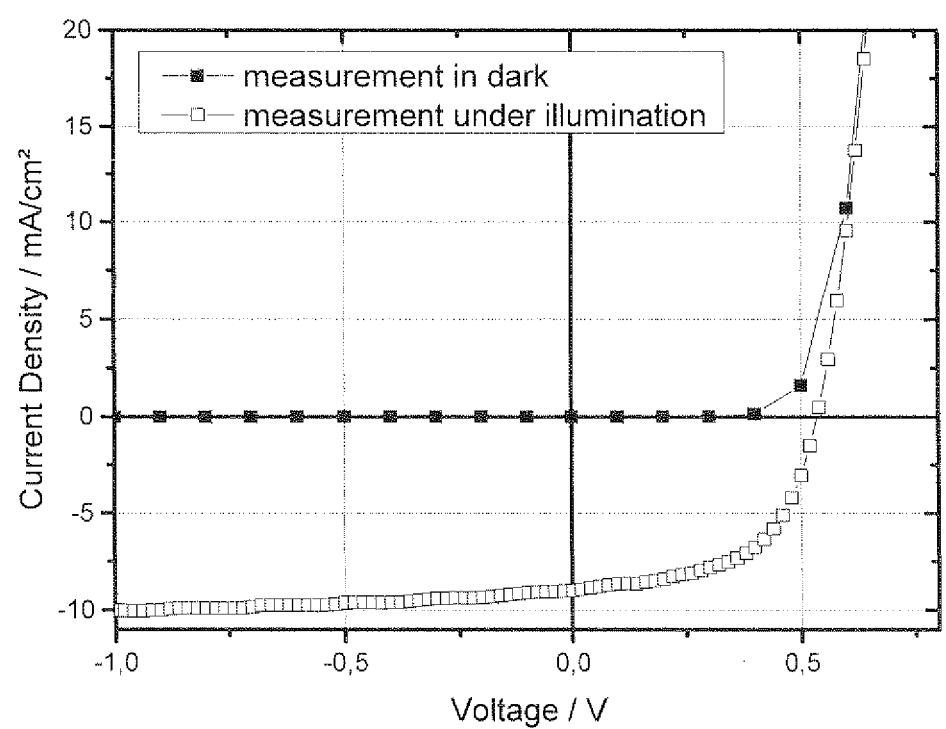
FIG. 3 is a schematic diagram of a solar cell used in the Device example 2

FIG. 4 is a current—voltage characteristics of an OSC according to Device example 2, comprising compound C13 as the n-dopant in the ETL According to FIG. 1, an organic solar cell comprises at least a substrate 10, an anode 11, a light absorbing unit 12, and a cathode 13. The stack of layers can also be inverted, wherein layer 11 would be the cathode, and layer 13 would be the anode. Additional light absorbing units can be provided in the organic solar cell.

In one embodiment, the substrate 10 can be a transparent substrate, such as a glass, or polymeric plate or web. The anode 11 can be a transparent conducting oxide, such as ITO, FTO, AlZO. The cathode 13 can comprise aluminum or an aluminum alloy. Alternatively, the light absorbing unit 12 can comprise a blend of a donor polymer, preferentially a thiophene containing polymer, and an acceptor, preferentially a fullerene or a soluble fullerene derivative. In this embodiment, an additional layer comprising the compound according to Formula 1 (such as a doped electron transport layer) or consisting of it (such as an electron extracting layer) is formed between the light absorbing unit 12 and the cathode 13. Optionally, the layer structure can be inverted.

In an alternative embodiment, the anode 11 is not transparent and mainly comprises aluminum or an aluminum alloy. The substrate 10 is not necessarily transparent. The cathode 13 comprises a transparent conducting oxide layer or a thin transparent metal layer having a thickness of less than 30 nm.

Still in connection to FIG. 1, in another embodiment, the substrate 10, the anode 11, and the cathode 13 are transparent. In this embodiment, the overall device is semi-transparent, because it does not have 100% absorption of the incident light for any wavelength in the visible range of wavelengths.

Multiple stacked devices (e.g. tandem devices) can also be provided. In such devices, at least one additional light absorbing unit is formed between the light absorbing unit 12 and the cathode 13. Additional organic or inorganic layers may be formed to provide a suitable electronic connection and optical optimization of the layer position. Preferentially, at least parts of these functions are provided by layers comprising a compound according to the Formula 1.

Figure 2:
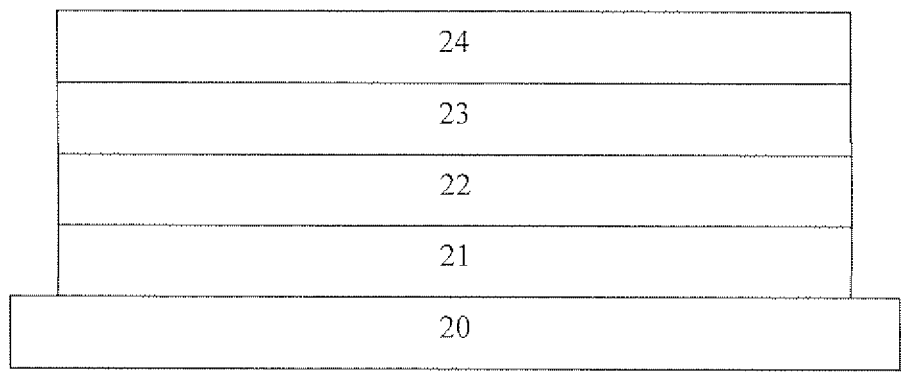
FIG. 2 is a schematic diagram representing a stack of layers of a solar cell comprising an electron transport layer (ETL).

FIG. 2 shows a stack of layers representing an organic solar cell comprising a substrate 20, an anode 21, a light absorbing unit 22 comprising an absorption layer, an organic electron transport layer (ETL) 23, and a cathode 24. The stack of layers can also be inverted. The ETL can be formed between the cathode 24 and the absorption layer 22. Additional light absorbing units can be provided in the solar cell.

In one embodiment, the organic electron transport layer 23 can comprise as its main component an electron transport matrix (ETM) compound and the compound according to the Formula 1 as a dopant. The doped ETL 23 can have any thickness. Its thickness is preferably smaller than 50 nm in the case that there is no additional absorption layer between the light absorbing layer 22 and the cathode 24.

All embodiments as described in connection to FIG. 1 can also be applied for the solar cell according to FIG. 2.

All figures are schematic representations of the layered structure of a solar cell. Some device features are not shown such as electrical connections, encapsulation, optical structures which are external to the electrodes, etc. The layer thicknesses are not drawn to scale. At least one of the electrodes (anode and/or cathode) is transparent in the wavelength range in which the device is active.

In another embodiment, the light absorbing unit 22 is a donor-acceptor bulk heterojunction, e.g. a blend of donor-acceptor materials. The donor is preferentially formed by a strong absorbing compound comprising a pyrrole or a thiophene group. The acceptor is preferentially a $C_{58}$, $C_{60}$, or $C_{70}$ fullerene or a soluble fullerene derivative. The ETL 23 can comprise a compound according to the Formula 1 as a dopant.

In Table 1, preferred exemplary compounds according to Formula 1 are listed together with conductivities achieved if 10 wt. % of an inventive compound has been doped into one of ETMs E1, E2, E3. HOMO values were measured by cyclic voltammetry in dichloromethane (DCM), the values with asterisk in tetrahydrofuran (THF), n.s. means "no signal".

E1 stands for the fullerene $C_{60}$ (CAS 99685-96-8, LUMO −1.0 V vs $Fc^+$/Fc, see Chem. Rev. 2000, vol. 100, p. 1075, Table 1),

TABLE 1

E2 for

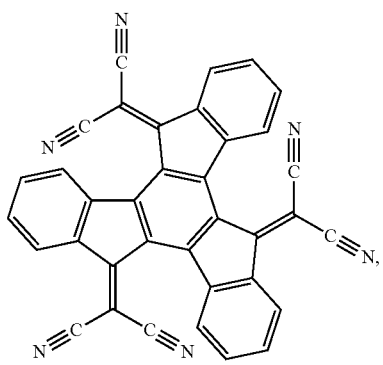

(CAS 256642-92-9, LUMO -0.83 V vs $Fc^+$/Fc)

E3 for

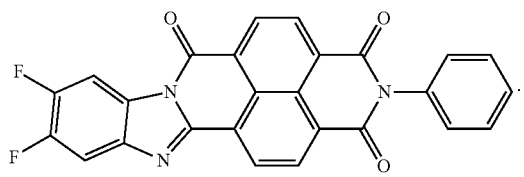

(CAS 1415745-03-7, reported in WO2012/16838, LUMO -1.01 V vs $Fc^+$/Fc)

| dopant | Dopant formula | HOMO (CV) V | Conductivity in given matrix $10^{-5}$ S · cm$^{-1}$ | | |
|---|---|---|---|---|---|
| | | | E1 | E2 | E3 |
| C1 | 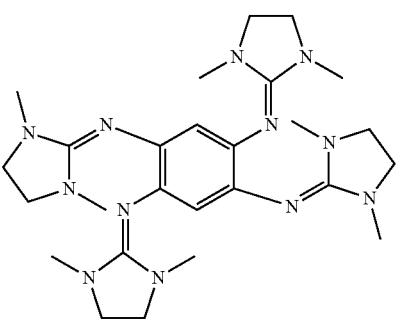 [SMILES: CN1CCN(C)C1=Nc1cc(N=C2N(C)CCN2C)c(N=C2N(C)CCN2C)cc1N=C1N(C)CCN1C] | −0.79 | | | |

TABLE 1-continued
E2 for
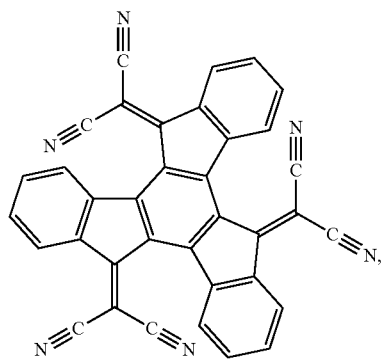
(CAS 256642-92-9, LUMO -0.83 V vs Fc$^+$/Fc)
E3 for
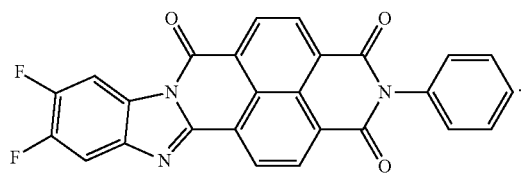
(CAS 1415745-03-7, reported in WO2012/16838, LUMO -1.01 V vs Fc$^+$/Fc)
| dopant | Dopant formula | HOMO (CV) V | Conductivity in given matrix $10^{-5}$ S · cm$^{-1}$ | | |
|---|---|---|---|---|---|
| | | | E1 | E2 | E3 |
| C2 | | -0.40 -0.37* | | | |
| C3 | | -0.39 | | | |

TABLE 1-continued
E2 for
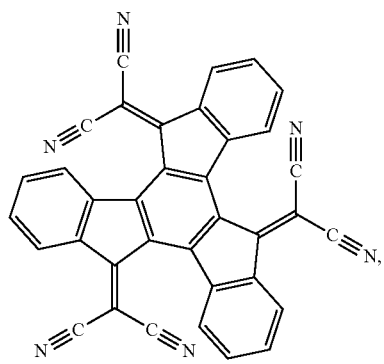
(CAS 256642-92-9, LUMO -0.83 V vs Fc$^+$/Fc)
E3 for
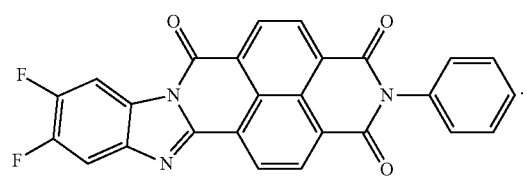
(CAS 1415745-03-7, reported in WO2012/16838,
LUMO -1.01 V vs Fc$^+$/Fc)
| dopant | Dopant formula | HOMO (CV) V | Conductivity in given matrix $10^{-5}$ S · cm$^{-1}$ | | |
|---|---|---|---|---|---|
| | | | E1 | E2 | E3 |
| C4 | | −0.76 | 8750 142** | | |
| C5 | | −0.34 | | | |
| C6 | | −0.21 | 36 170** | 0.0004 | 0.007 |

TABLE 1-continued
E2 for
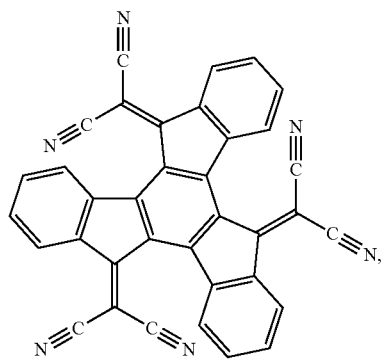
(CAS 256642-92-9, LUMO -0.83 V vs Fc$^+$/Fc)
E3 for
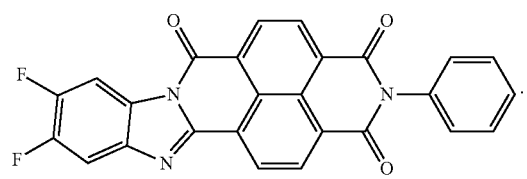
(CAS 1415745-03-7, reported in WO2012/16838, LUMO -1.01 V vs Fc$^+$/Fc)
| dopant | Dopant formula | HOMO (CV) V | Conductivity in given matrix $10^{-5}$ S · cm$^{-1}$ | | |
|---|---|---|---|---|---|
| | | | E1 | E2 | E3 |
| C7 | | −0.64 | 2430 157** | 4 132 | 0.4 115 |
| C8 | | −0.46 | 157 136** | 0.04 147** | |

TABLE 1-continued
E2 for
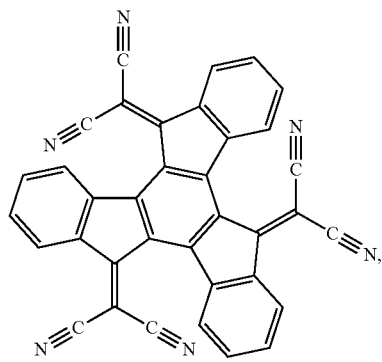
(CAS 256642-92-9, LUMO -0.83 V vs Fc$^+$/Fc)
E3 for
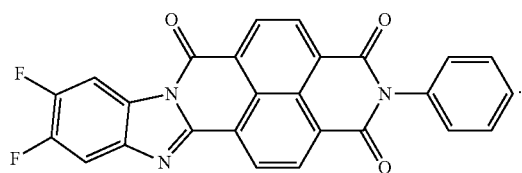
(CAS 1415745-03-7, reported in WO2012/16838, LUMO -1.01 V vs Fc$^+$/Fc)
| dopant | Dopant formula | HOMO (CV) V | Conductivity in given matrix $10^{-5}$ S · cm$^{-1}$ | | |
|---|---|---|---|---|---|
| | | | E1 | E2 | E3 |
| C9 | 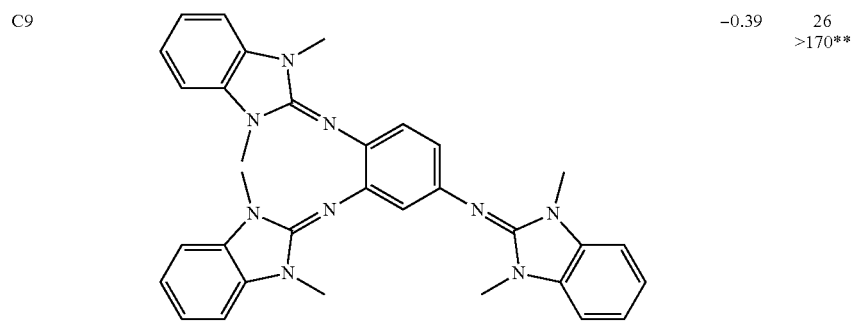 | −0.39 | 26 >170** | | |

TABLE 1-continued
E2 for
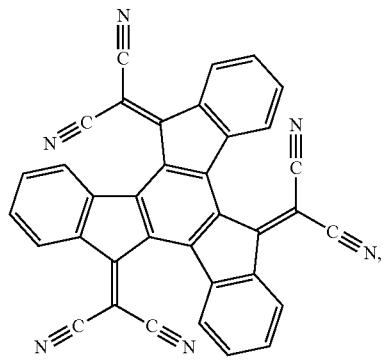
(CAS 256642-92-9, LUMO -0.83 V vs Fc$^+$/Fc)
E3 for
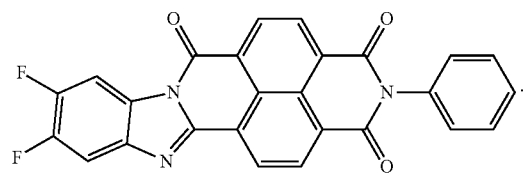
(CAS 1415745-03-7, reported in WO2012/16838, LUMO -1.01 V vs Fc$^+$/Fc)
| dopant | Dopant formula | HOMO (CV) V | Conductivity in given matrix $10^{-5}$ S · cm$^{-1}$ | | |
|---|---|---|---|---|---|
| | | | E1 | E2 | E3 |
| C10 | | −0.37 | 6.5 >170** | | |
| C11 | | −0.60 | | | |

TABLE 1-continued
E2 for
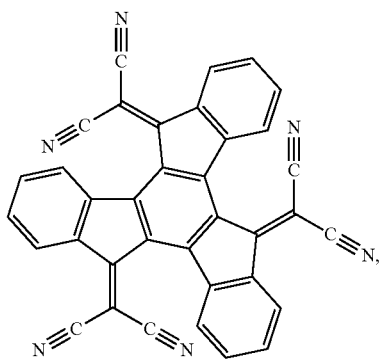
(CAS 256642-92-9, LUMO -0.83 V vs Fc$^+$/Fc)
E3 for
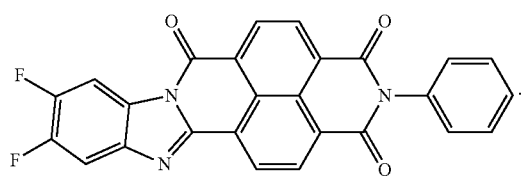
(CAS 1415745-03-7, reported in WO2012/16838, LUMO -1.01 V vs Fc$^+$/Fc)
| dopant | Dopant formula | HOMO (CV) V | Conductivity in given matrix $10^{-5}$ S · cm$^{-1}$ | | |
|---|---|---|---|---|---|
| | | | E1 | E2 | E3 |
| C12 | | −0.13* | 40 170** | | |
| C13 | | n.s.* | 7 122** | | |

TABLE 1-continued
E2 for
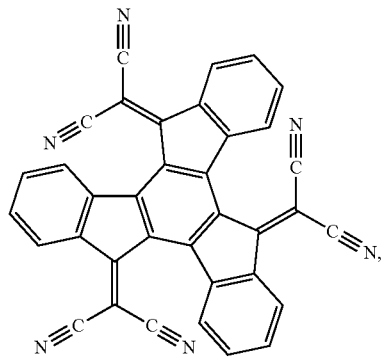
(CAS 256642-92-9, LUMO -0.83 V vs Fc$^+$/Fc)
E3 for
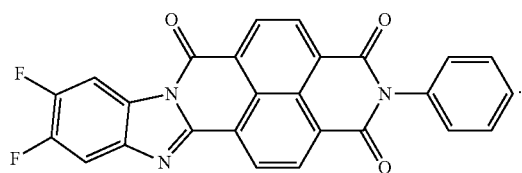
(CAS 1415745-03-7, reported in WO2012/16838,
LUMO -1.01 V vs Fc$^+$/Fc)
| dopant | Dopant formula | HOMO (CV) V | Conductivity in given matrix $10^{-5}$ S · cm$^{-1}$ | | |
|---|---|---|---|---|---|
| | | | E1 | E2 | E3 |
| C14 | 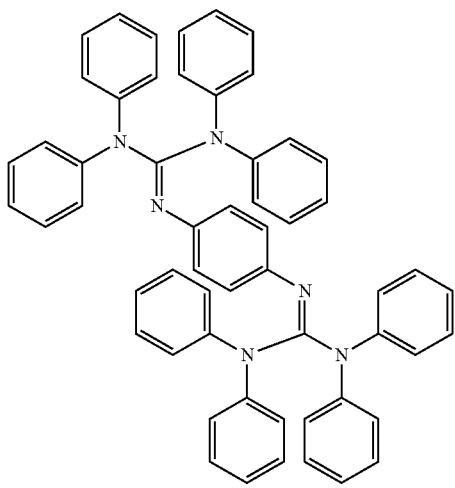 [SMILES: c1ccc(N(C(=Nc2ccc(N=C(N(c3ccccc3)c3ccccc3)N(c3ccccc3)c3ccccc3)cc2)N(c2ccccc2)c2ccccc2)c2ccccc2)cc1] | | 0.17* | 0.3 163** | |

TABLE 1-continued
E2 for
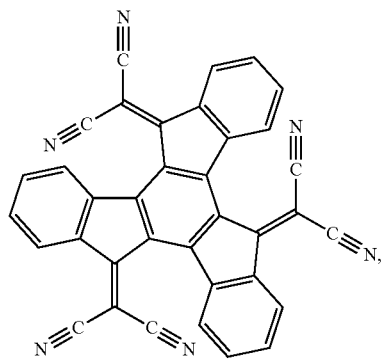
(CAS 256642-92-9, LUMO -0.83 V vs Fc$^+$/Fc)
E3 for
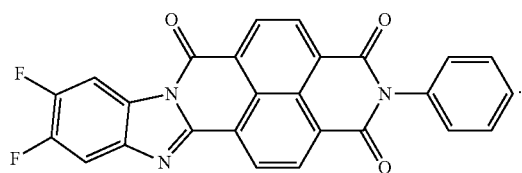
(CAS 1415745-03-7, reported in WO2012/16838, LUMO -1.01 V vs Fc$^+$/Fc)
| | | HOMO (CV) | Conductivity in given matrix $10^{-5}$ S · cm$^{-1}$ | | |
|---|---|---|---|---|---|
| dopant | Dopant formula | V | E1 | E2 | E3 |
| C15 | | n.s.* | 1.5 >170** | | |

The second value listed below certain conductivity values and highlighted with double asterisk gives the temperature of maximum conductivity in ° C. If the temperature rises above this value, gradual conductivity decrease is observed. In OPV, it is advantageous if the maximum conductivity temperature is higher than 100° C. Preferably, it is higher than 110° C., more preferably higher than 120° C., even more preferably higher than 130° C., most preferably higher than 140° C. The obtained results showed that the provided compounds allow an efficient n-doping in typical ETMs used in OPV, with very good temperature stability of conductivity.

EXAMPLES

Auxiliary Procedures

The syntheses were done with commercially available starting compounds and anhydrous solvents that were not additionally purified. $^{13}$C NMR spectra were measured at 125 MHz in deuterochloroform as solvent.

Cyclic Voltammetry

The redox potentials given at particular compounds were measured in an argon deaerated, dry 0.1M THF solution of the tested substance, under argon atmosphere, with 0.1M tetrabutylammonium hexafluorophosphate supporting electrolyte, between platinum working electrodes and with an Ag/AgCl pseudo-standard electrode, consisting of a silver wire covered by silver chloride and immersed directly in the measured solution, with the scan rate 100 mV/s. The first run was done in the broadest range of the potential set on the working electrodes, and the range was then adjusted within subsequent runs appropriately. The final three runs were done with the addition of ferrocene (in 0.1M concentration) as the standard. The average of potentials corresponding to cathodic and anodic peak of the studied compound, after subtraction of the average of cathodic and anodic potentials observed for the standard Fc$^+$/Fc redox couple, afforded finally the values reported above.

Synthesis Example 1

N-(chloro(dimethylamino) methylene)-N-methylmethanaminium chloride (I2)

37.8 mL (440 mmol) oxalyl dichloride were added slowly to a solution of 10.5 mL (88 mmol) 1,1,3,3-tetramethylurea in 60 mL chloroform under argon atmosphere. After stirring for 16 hours at 85° C. (under reflux), the solvent was distilled off and the residue washed with diethyl ether. After drying in vacuo, 14.9 g (87.6 mmol; 99.5%) N-(chloro (dimethylamino) methylene)-N-methylmethanaminium chloride were obtained.

Synthesis Example 2

2-chloro-1,3-dimethyl-1H-benzo[d]imidazol-3-ium hexafluoro phosphate (I3)

To 12.5 g (81.9 mmol) 2-chloro-1H-benzo[d]imidazole in 175 ml water, 20.6 g (245.7 mmol) sodium hydrogen carbonate and 46.6 mL (491.5 mmol) dimethyl sulphate were added. The mixture was stirred 10 hours at 80° C. After cooling to 0° C., 30 mL hydrogen hexafluoro phosphate(V) were added. Filtration of the precipitate, washing with water and drying in vacuo gave 14.84 g (45.44 mmol; 55%) 2-chloro-1,3-dimethyl-1H-benzo[d]imidazol-3-ium hexafluoro phosphate.

Synthesis Example 3

1-(chloro(piperidin-1-yl)methylene)piperidin-1-ium chloride (I4)

33 mL (38.4 mmol) oxalyl dichloride were added slowly to 15.3 g (7.8 mmol) di(piperidin-1-yl)methanone in 150 mL chloroform under argon atmosphere. The mixture was stirred for 20 hours at 80° C. After distillation of the solvent and drying in vacuo, the 1-(chloro(piperidin-1-yl)methylene)piperidin-1-ium chloride was used for the next synthesis step without further purification.

Synthesis Example 4

1,4-phenylene diimidophosgene intermediate (I6)

Into a stirred solution of 50.00 g 1,4-phenylene diisocyanate in 250 mL chloroform kept by means of an ice cooling bath at the temperature between 0 and 25° C., dry gaseous chlorine has been introduced during approximately 1 hour, until the gas absorption ceased. After additional 3 hours stirring at RT, the solution was rotary evaporated to afford 71 g light grey crystalline solid which was crystallized from 700 mL EE. Obtained 61.3 g white crystalline solid. LC/MS 270 (M).

Synthesis Example 5

N1,N2,N4,N5-tetrakis(1,3-dimethylimidazolidin-2-ylidene)benzene-1,2,4,5-tetraamine (C1)

1.49 g (8.8 mmol) 2-chloro-1,3-dimethyl-4,5-dihydro-1H-imidazol-3-ium chloride (commercially available intermediate I1) in 24 mL acetonitrile were added to a suspension of 0.5 g (1.76 mmol) benzene-1,2,4,5-tetraamine tetrahydrochloride in 10 mL acetonitrile and 3.2 mL triethylamine at 0° C. under argon atmosphere. The mixture was stirred for 1.5 hours at 0° C. After filtration of the formed precipitate and distillation of the solvent, the residue was dissolved in aqueous hydrochloric acid (having 10 wt. % concentration) and alkalized with aqueous sodium hydroxide (20 wt. %). The precipitate was filtered, washed with water and dried in vacuo to give 0.92 g (1.76 mmol; 100% of theoretical yield) white solid. The product was purified by gradient sublimation for analytical characterisation.

Melting point: 290° C.

Synthesis Example 6

N3,N3',N4,N4'-tetrakis(1,3-dimethylimidazolidin-2-ylidene)-[1,1'-biphenyl]-3,3',4,4'-tetraamine (C2)

2.00 g (11.83 mmol) 2-chloro-1,3-dimethyl-4,5-dihydro-1H-imidazol-3-ium chloride (I1) in 10 mL acetonitrile were added to a suspension of 0.61 g (2.85 mmol) biphenyl-3,3',4,4'-tetraamine in 20 mL acetonitrile and 4.6 mL triethylamine under argon atmosphere. The mixture was stirred for 2 days at room temperature. After filtration of the precipitate and distillation of the solvent, the residue was suspended in 2 M sodium hydroxide solution and stirred for 5 minutes at 45° C. 1.17 g (1.95 mmol; 68%) off-white solid were obtained after filtration, washing with water and drying in vacuo. The product was purified by gradient sublimation for analytical characterisation.

Melting point: 231° C.

Synthesis Example 7

N1-(1,3-dimethylimidazolidin-2-ylidene)-N4,N4-bis(4-((1,3-dimethylimidazolidin-2-ylidene)amino)phenyl)benzene-1,4-diamine (C3)

2.00 g (11.9 mmol) 2-chloro-1,3-dimethyl-4,5-dihydro-1H-imidazol-3-ium chloride (I1) in 20 mL acetonitrile were added to a suspension of 1.00 g (3.4 mmol) N1,N1-bis(4-aminophenyl)benzene-1,4-diamine in 30 mL acetonitrile and 3.8 mL triethylamine under argon atmosphere. The mixture was stirred for 24 hours at room temperature. After distillation of the solvent, the residue was suspended in 2 M sodium hydroxide solution and stirred for 5 minutes at 45° C. 1.4 g (2.42 mmol; 71%) rose solid were obtained after filtration, washing with water and acetone and drying in vacuo. The product was purified by gradient sublimation for analytical characterisation.
Melting point: 226° C.

Synthesis Example 8

2',2''',2''''-(benzene-1,2,4,5-tetrayl)tetrakis(1,1,3,3-tetramethylguanidine) (C4)

14.9 g (87.6 mmol) N-(chloro(dimethylamino)methylene)-N-methylmethanaminium chloride (I2) in 250 mL acetonitrile were added to a suspension of 5 g (17.6 mmol) benzene-1,2,4,5-tetraamine tetrahydrochloride in 100 mL acetonitrile and 51 mL triethylamine at 0° C. under argon atmosphere. The mixture was stirred for 2 hours at 0° C. After distillation of the solvent, the residue was dissolved in aqueous hydrochloric acid (10 wt. %) and alkalized with 20 wt. % aqueous sodium hydroxide. Extraction with toluene, washing with acetonitrile and drying in vacuo gave 3.16 g (5.96 mmol; 34%) white solid. The product was purified by gradient sublimation for analytical characterisation.
Melting point: 206° C.

Synthesis Example 9

N1,N4-bis(1,3-dimethylimidazolidin-2-ylidene)-2-methoxybenzene-1,4-diamine (C5)

1$^{st}$ Step
3.0 g (17.8 mmol) 2-methoxy-4-nitroaniline and 0.8 g palladium on charcoal (10 wt. %) were added to 100 ml tetrahydrofuran (THF). 8.66 mL (114 mmol) hydrazine monohydrate in 40 ml THF were cautiously added and the reaction mixture was stirred at 90° C. for 3 hours. After cooling, the suspension was filtered and the collected solid washed with THF. The filtrate was reduced to a gray residue under reduced pressure. 2.44 g (17.66 mmol, 99%) 2-methoxybenzene-1,4-diamine were stored under argon and used without further purification.
2$^{nd}$ Step
2.00 g (11.9 mmol) 2-chloro-1,3-dimethyl-4,5-dihydro-1H-imidazol-3-ium chloride (I1) in 20 mL acetonitrile were added to a suspension of 0.66 g (4.7 mmol) 2-methoxybenzene-1,4-diamine in 20 mL acetonitrile and 2.4 mL triethylamine under argon atmosphere. The mixture was stirred for 50 hours at room temperature. After filtration of the precipitate and distillation of the solvent, the residue was suspended in 2 M aqueous sodium hydroxide solution and stirred for 5 minutes at 45° C. The precipitate was filtered, the solvent distilled off, the residue suspended in acetonitrile/methanol mixture and filtered through an alumina pad (Polygram® Alox N/UV$_{254}$). 1.2 g (3.63 mmol; 77%) orange solid were obtained after drying in vacuo. The product was purified by gradient sublimation for analytical characterisation.
Melting point: 149° C.

Synthesis Example 10

N1,N4-bis(1,3-dimethyl-1H-benzo[d]imidazol-2(3H)-ylidene)benzene-1,4-diamine (C6)

14.84 g (45.44 mmol) 2-chloro-1,3-dimethyl-1H-benzo[d]imidazol-3-ium hexafluoro phosphate (I3) in 50 mL acetonitrile were added to a suspension of 1.97 g (18.18 mmol) benzene-1,4-diamine in 250 mL acetonitrile and 15.7 mL triethylamine under argon atmosphere at 0° C. The mixture was stirred for 20 hours at room temperature. The precipitate was filtered, washed with acetonitrile, suspended in 2 M sodium hydroxide solution and stirred for 5 minutes at 45° C. 6.42 g (11.65 mmol; 64%) white solid was obtained after filtration, washing with water and drying in vacuo. The product was purified by gradient sublimation for analytical characterisation.
Melting point: 290° C.

Synthesis Example 11

N1,N2,N4,N5-tetrakis(1,3-dimethyl-1H-benzo[d]imidazol-2(3H)-ylidene)benzene-1,2,4,5-tetraamine (C7)

15.3 g (46.84 mmol) 2-chloro-1,3-dimethyl-1H-benzo[d]imidazol-3-ium hexafluoro phosphate (I3) in 50 mL acetonitrile were added to a suspension of 2.66 g (9.37 mmol) benzene-1,2,4,5-tetraamine tetrahydrochloride in 250 mL acetonitrile and 16 mL triethylamine under argon atmosphere. The mixture was stirred for 20 hours at room temperature. The precipitate was filtered, washed with acetonitrile, suspended in 2 M sodium hydroxide solution and stirred for 5 minutes at 45° C. 5.7 g (7.97 mmol; 85%) white solid was obtained after filtration, washing with water and drying in vacuo. The product was purified by gradient sublimation for analytical characterisation.
Melting point: 374° C.

Synthesis Example 12

N1,N2,N4-tris(di(piperidin-1-yl)methylene)benzene-1,2,4-triamine (C8)

19.6 g (78 mmol) 1-(chloro(piperidin-1-yl)methylene)piperidin-1-ium chloride (I4) in 150 mL acetonitrile and 65 mL triethylamine were added to a suspension of 5.1 g (26 mmol) benzene-1,2,4-triamine dihydrochloride in 160 mL acetonitrile and 22 mL triethylamine under argon atmosphere. The mixture was stirred for 72 hours at room temperature. The precipitate was filtrated and the solvent distilled off. The residue was purified by column chromatography in chloroform/methanol and by precipitation in hexane from a dichloromethane solution, to give 2 g (3.04 mmol; 12%) foamy solid. The product was purified by gradient sublimation for analytical characterisation.

Synthesis Example 13

N1,N2,N4-tris(1,3-dimethyl-1H-benzo[d]imidazol-2(3H)-ylidene)benzene-1,2,4-triamine (C9)

11.7 g (35.83 mmol) 2-chloro-1,3-dimethyl-1H-benzo[d]imidazol-3-ium hexafluoro phosphate (I3) in 25 mL acetonitrile were added to a suspension of 1.79 g (9.13 mmol) benzene-1,2,4-triamine dihydrochloride in 40 mL acetonitrile and 12.7 mL triethylamine under argon atmosphere at 0° C. The mixture was stirred for 72 hours at room temperature. The precipitate was filtered, washed with acetonitrile, suspended in 2 M sodium hydroxide solution and stirred for 5 minutes at 45° C. 2.5 g (4.5 mmol; 49%) grey solid were obtained after filtration, washing with water and acetonitrile and drying in vacuo. The product was purified by gradient sublimation for analytical characterisation.

Synthesis Example 14

N1-(1,3-dimethyl-1H-benzo[d]imidazol-2(3H)-ylidene)-N4,N4-bis(4-((1,3-dimethyl-1H-benzo[d]imidazol-2(3H)-ylidene)amino)phenyl)benzene-1,4-diamine (C10)

3.15 g (9.65 mmol) 2-chloro-1,3-dimethyl-1H-benzo[d]imidazol-3-ium hexafluorophosphate (I3) in 25 mL acetonitrile were added to a suspension of 0.75 g (2.57 mmol) N1,N1-bis(4-aminophenyl)benzene-1,4-diamine in 75 mL acetonitrile and 3.2 mL triethylamine under argon atmosphere at 0° C. The mixture was stirred for 48 hours at room temperature. The precipitate was filtered, washed with acetonitrile, suspended in 2 M aqueous sodium hydroxide solution and stirred for 5 minutes at 45° C. 0.9 g (1.25 mmol; 49%) foamy solid was obtained after filtration, washing with water and drying in vacuo. The product was purified by gradient sublimation for analytical characterisation.

Synthesis Example 15

3,3'-(1,4-phenylenebis(azanylylidene))bis(N1,N1,N2,N2-tetramethylcycloprop-1-ene-1,2-diamine) (C11)

A 25 ml flask was charged with 10 mL of acetonitrile, 1 g (2 mmol) of chloro bis(dimethylamino) cyclopropylium hexachloroantimonate (commercially available intermediate I5) and 0.6 mL 1.8 diazabicyclo[5.4.0]undec-7-ene. Diamino benzene (86 mg, 0.8 mmol) was added and the resulting mixture was kept at 90° C. overnight. After cooling, the suspension was filtered and the dark filter cake was washed with acetonitrile. The filtrate was concentrated in vacuo to afford red oil that was dissolved in dichloromethane. The organic layer was washed with diluted sodium hydroxide solution and two times with water. After drying with magnesium sulphate, the solvent was removed in vacuum. 54 mg (19%) yellowish solid were isolated.

Synthesis Example 16

N,N'-Bis-(di-morpholin-4-yl-methylene)-benzene-1,4-diamine (C12)

8.10 g (30 mmol, 1 eq) 1,4-phenylene diimidophosgene intermediate (I6) was dissolved under nitrogen in 150 mL dry THF, 42 mL (480 mmol, 16 eq) morpholine added under cooling in an ice bath (exothermic), 16 h stirred at RT, white suspension evaporated under vacuum on rotary evaporator, 75 mL morpholine added, heated for 5 h in a 110° C. hot oil bath, the suspension turned brown-yellow, stirred at RT for additional 16 h. The reaction mixture has been dissolved in 750 mL chloroform, extracted with 375 mL 2M aqueous NaOH, the aqueous phase extracted twice with 375 mL chloroform, combined organic phase extracted with 188 mL 2M NaOH and 375 mL brine, dried with sodium sulphate and rotary evaporated, affording 15.5 g of light brown solid. The crude product was purified by boiling with 150 mL absolute ethanol, the suspension cooled to RT, filtered, washed with absolute ethanol and dried in vacuum. Obtained 13.69 g white solid comprising according to NMR probe 96% purity with 4% solvent, further purified by crystallization from isopropyl alcohol.

Elemental analysis: C, 60.79% (theor. 61.00), H, 7.55% (theor. 7.68), N, 17.64% (theor. 17.78). LC/MS-ESI 473 (M+H), $^{13}$C-NMR: 48.80, 66.75, 122.31, 144.46 and 157.09 ppm.

Synthesis Example 17

N"-[4-(N',N"-Dimethyl-N',N"-diphenyl-guanidino)-phenyl]-N,N'-dimethyl-N,N'-diphenyl-guanidine (C13)

5.40 g (20 mmol, 1 eq) 1,4-phenylene diimidophosgene intermediate (I6) was mixed under nitrogen with 34.6 mL neat N-methylaniline (320 mmol, 16 eq) to form a greenish suspension without an exothermic effect. Under heating, an exothermic reaction starts at 60° C., the mixture solidified during cca 30 min at 90° C. Cooled down, suspended with an ultrasound bath in 150 mL diethyl ether, light grey solid filtered, dissolved in 300 mL chloroform, extracted with 160 mL 1M aqueous NaOH, the aqueous phase extracted twice with 50 mL chloroform, combined organic extracts washed with 100 mL 1 M NaOH and 100 mL brine, dried over sodium sulphate, filtered and the filtrate rotary evaporated under vacuum. Obtained 18.2 g light pink solid, purified by boiling with toluene and, subsequently, with ethanol and chloroform, to afford a white solid finally purified by crystallization from isopropyl alcohol.

Elemental analysis: C, 77.79% (theor. 78.23), H, 6.53% (theor. 6.57), N, 15.11% (theor. 15.20). LC/MS-APCI 552 (M), $^{13}$C-NMR: 39.63, 117.41, 120.15, 122.10, 123.81, 128.51 and 153.79 ppm.

Synthesis Example 18

N,N,N',N'-Tetraphenyl-N"-[4-(N',N',N",N"-tetraphenyl-guanidino)-phenyl]-guanidine (C14)

5.00 g (18.5 mmol, 1 eq) 1,4-phenylene diimidophosgene intermediate (I6) was mixed under nitrogen with 50.143 g neat diphenyl amine (296 mmol, 16 eq) molten by heating the reaction flask in a 70° C. warm oil bath. After one hour at 100° C., the originally yellow-green homogeneous mixture turned brown. Cooled down to RT, mixed with 50 mL diethyl ether, treated with ultrasound, until the oily viscous mixture turned into a yellow suspension. 100 mL saturated aqueous NaHCO$_3$ added, the orange-brown organic phase separated, the aqueous phase extracted twice with 50 mL EE, combined organic phases extracted with 50 mL saturated aqueous NaHCO$_3$ and rotary evaporated to form 47 g yellow oil that after addition 300 mL EE formed in the ultrasound bath a fine suspension, which after filtration and drying afforded 6.26 g of a yellow solid. The crude product has been further purified by subsequent crystallizations from toluene and isopropyl alcohol.

Elemental analysis: C, 83.80% (theor. 83.97), H, 5.63% (theor. 5.54), N, 10.40% (theor. 10.49). LC/MS-ESI 801 (M+H), $^{13}$C-NMR: 121.28, 123.88, 124.10, 124.33, 125.00, 128.54, 128.69, 143.22, 144.30, 144.86, 150.50 ppm.

Synthesis Example 19

N''-[4-(N',N',N'',N''-Tetra-p-tolyl-guanidino)-phenyl]-N,N,N',N'-tetra-p-tolyl-guanidine (C15)

5.24 g (20.0 mmol, 1 eq) 1,4-phenylene diimidophosgene intermediate (I6) was mixed under nitrogen with 63.13 g neat p,p'-ditolyl amine (320 mmol, 16 eq) molten by heating the reaction flask a 85° C. warm oil bath. After three hours at 100° C. the brown solution has been cooled down, diluted with 500 mL chloroform and agitated with 250 mL 2M aqueous NaOH. The organic phase was separated, the aqueous phase was extracted twice with 250 mL chloroform, the combined organic phases were extracted subsequently with 250 mL 2M NaOH, 250 mL brine, dried over sodium sulphate and rotary evaporated to afford 70 g viscous substance that was dissolved in 300 mL EE, concentrated, dissolved in 200 mL boiling ethanol, and crystallized by cooling to RT. Obtained crude product has been chromatographed on a silica column with EE:petrolether as eluent, to afford 6.97 g yellow crystalline solid. $^{13}$C-NMR: 20.84, 20.92, 121.17, 122.53, 123.85, 124.70, 128.35, 128.93, 129.14, 132.29, 132.96, 133.52, 139.73, 142.08, 142.60, 143.15, 143.30, 146.02, 150.79 ppm.

In device examples, following auxiliary compounds were used:
N4,N4,N4'',N4''-tetra([1,1'-biphenyl]-4-yl)-[1,1':4',1''-terphenyl]-4,4''-diamine (HT1, CAS 925431-34-4) as a hole transport matrix, 1,2,3-triylidenetris(cyanomethanylylidene))tris-(2,3,5,6-tetrafluorobenzonitrile)-cyclopropane (PD2, CAS 1224447-88-4), tetrakis (1,3,4,6,7,8-hexahydro-2H-pyrimido[1,2-a]pyrimidinato) ditungsten (II) ($W_2(hpp)_4$, CAS 463931-34-2)

Device Example 1

A pn junction device was used to benchmark the new dopants according to Formula 1 with the strong donor $W_2(hpp)_4$. The pn-junction device was made on a glass substrate using ITO as anode, a 50 nm p-doped HTL (hole transport layer) consisting of the hole transport matrix HT1 and p-dopant PD2 in weight ratio 9:1, a 50 nm electron transport layer consisting of fullerene $C_{60}$ as matrix, doped with one of the new dopants according to Formula 1 in weight ratio 7:3, and an Al cathode. The voltage necessary for a current density of 5 mA/cm$^2$ was 0.02 V for compound C7, 0.64 V for compound C12, 0.65 V for compound C13, 0.30 V for compound C14 and 0.78 V for compound C15. The value for compound C7 is surprisingly good, given the much lower donating strength in comparison with $W_2(hpp)_4$ (HOMO<<−1.0 V vs Fc$^+$/Fc), which in the same arrangement allowed to operate the pn junction at the voltage of 0.01 V for the current density of 5 mA/cm$^2$. Compounds C12-C15, having even lower reduction strength in terms of their redox potentials listed in the Table 1, still allowed the operation of the pn junction at voltages below 1 V.

Device Example 2

The layer structure of the experimental photovoltaic device designed for assessment of the applicability of the imine compounds of the present invention in semiconducting materials is schematically shown as FIG. 3. The device was prepared on the glass substrate 30 bearing a 90 nm ITO cathode 31, by vacuum deposition of the following layers: 10 nm thick ETL 32 made of fullerene $C_{60}$ doped with a compound of Formula 1 in a weight ratio 9:1, 20 nm thick absorption layer 33 made of $C_{60}$, 30 nm thick absorption layer 34 made of $C_{60}$ and zinc phtalocyanine in weight ratio 1:1, 2 nm thick hole extraction layer 35 made of HT1, 40 nm thick HTL 36 made of HT1 doped with PD2 in weight ratio 19:1, 2 nm thick hole injection layer 37 made of neat PD2 and 100 nm thick aluminium anode 38. Comparison of performance of the device for several inventive electron transport materials gives the Table 2.

TABLE 2

| dopant | Voc (V) | Jsc (mA/cm$^2$) | fill factor (%) | saturation | efectivity (%) |
|---|---|---|---|---|---|
| C7 | 0.53 | 9.1 | 56 | 1.12 | 2.7 |
| C12 | 0.53 | 8.9 | 56 | 1.13 | 2.6 |
| C13 | 0.53 | 9.0 | 56 | 1.12 | 2.7 |

The obtained results surprisingly show that even the compounds of Formula 1 that have less negative redox potentials than −0.3 V vs Fc$^+$/Fc can be successfully used in semiconducting materials for OSCs.

The features of the invention disclosed in the above specification, the claims and the drawing may be important individually as well as in any combination for the implementation of the invention in its various embodiments.

Abbreviations Used Throughout the Application
AlZO aluminium zinc oxide
APCI atmospheric pressure chemical ionization
CAS Chemical Abstract Service reference number
CV cyclic voltammetry
DCM dichloromethane
EE diethyl ether
EIL electron injection/extraction layer
ESI electrospray ionization
ETL electron transport layer
ETM electron transport matrix
Fc ferrocene
Fc$^+$ ferrocenium
FTO fluorine-doped tin oxide
HBL hole blocking layer
HIL hole injecting layer
HOMO highest occupied molecular orbital
HPLC high performance liquid chromatography
HTL hole transport layer
HTM hole transport matrix
ITO indium tin oxide
LC liquid chromatography
LUMO lowest unoccupied molecular orbital
mol. % molar percent
MS mass spectrometry
NMR nuclear magnetic resonance
OLED organic light emitting diode
OPV organic photovoltaics
OSC organic solar cell
OVPD organic vapor phase deposition
QE quantum efficiency
PCBM phenyl C61 Butyric Acid Methyl Ester
R$_f$ retardation factor in TLC
TCNQ tetracyanoquinodimethane
T$_g$ glass transition temperature
TLC thin layer chromatography
vs versus
VTE vacuum thermal evaporation
wt. % weight percent

The invention claimed is:

1. Organic electronic device comprising a compound having Formula 1

$$AB_x \quad (1),$$

wherein
A is a structural moiety that consists of at least two atoms and comprises a conjugated system of delocalized electrons,
each B is independently selected from an imine functional group (Ia)

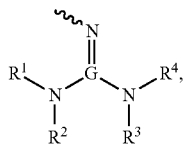

(Ia)

wherein $R^1$, $R^2$, $R^3$, $R^4$ are independently selected from $C_1$-$C_{30}$ alkyl, $C_2$-$C_{30}$ alkenyl, $C_2$-$C_{30}$ alkenyl, $C_3$-$C_{30}$ cycloalkyl, $C_6$-$C_{30}$ aryl, $C_2$-$C_{30}$ heteroaryl, $C_7$-$C_{30}$ arylalkyl, $C_3$-$C_{30}$ heteroarylalkyl,
the wave line represents a covalent bond to the imine nitrogen atom,
G is in each group (Ia) independently selected from a quarternary carbon atom and from a cyclopropenylidene structural moiety,
x is an integer equal to one or higher, and
the lone electron pair of the imine nitrogen atom and/or the pi-electrons of the imine double bond of at least one group B is conjugated with the conjugated system of delocalized electrons comprised in the structural moiety A,
with the proviso that two or more of the substituents $R^1$, $R^2$, $R^3$, $R^4$ may be connected to form a ring that may contain also unsaturation and, if any of the substituents $R^1$, $R^2$, $R^3$, $R^4$ comprises two or more carbon atoms, up to one third of the overall count of the carbon atoms in the substituent or in any ring formed by two connected substituents can be replaced with heteroatoms independently selected from O, S, N and B, and
wherein the device is a solar cell.

2. Organic electronic device according to claim 1, wherein x is an integer selected from 2, 3 and 4 and the lone electron pairs of the imine nitrogen atoms and/or the pi-electrons of the imine double bonds of at least two groups B are conjugated with the conjugated system of delocalized electrons comprised in the structural moiety A.

3. Organic electronic device according to claim 1, wherein A is a $C_3$-$C_{40}$ arene or $C_2$-$C_{40}$ heteroarene structural moiety that contains one conjugated system of delocalized electrons.

4. Organic electronic device according to claim 1, wherein A is a $C_6$-$C_{18}$ arene or $C_4$-$C_{18}$ heteroarene structural moiety and the lone electron pairs of the imine nitrogen atoms and/or the pi-electrons of the imine double bonds of all groups B are conjugated with the conjugated system of delocalized electrons comprised in the structural moiety A.

5. Organic electronic device according to claim 1, having a layered structure comprising several layers.

6. Organic electronic device according to claim 5, wherein the layer comprising the compound of Formula 1 is an electron transport layer or an electron injection layer.

7. Organic electronic device according to claim 5, wherein the layer comprising the compound of Formula 1 is an electron transport layer comprising an electron transport matrix and having a thickness of more than 50 nm, or a neat layer having a thickness less than 5 nm.

8. Organic electronic device according to claim 5, wherein the layer comprising the compound of Formula 1 is in direct contact to an electrode.

9. Organic electronic device according to claim 5, wherein a layer comprising the compound of Formula 1 is in direct contact to an electron transport layer.

10. Organic electronic device according to claim 5, wherein the layer comprising the compound of Formula 1 is part of a pn-junction connecting a light absorbing unit to an additional light absorbing unit in a tandem device or in a multiple stacked device and/or a pn-junction connecting a cathode or an anode to a light absorbing unit.

11. Organic electronic device according to claim 6, wherein the layer comprising the compound of Formula 1 is an electron transport layer comprising an electron transport matrix and having a thickness of more than 50 nm, or a neat layer having a thickness less than 5 nm.

12. Organic electronic device comprising:
a layered structure, wherein the layered structure comprises (i) an anode, (ii) a cathode, and (iii) a layer comprising an n-dopant arranged between the anode and the cathode;
wherein the n-dopant comprises a compound having Formula 1

$$AB_x \quad (1),$$

wherein
A is a structural moiety that consists of at least two atoms and comprises a conjugated system of delocalized electrons,
each B is independently selected from an imine functional group (Ia)

(Ia)

wherein $R^1$, $R^2$, $R^3$, $R^4$ are independently selected from $C_1$-$C_{30}$ alkyl, $C_2$-$C_{30}$ alkenyl, $C_2$-$C_{30}$ alkenyl, $C_3$-$C_{30}$ cycloalkyl, $C_6$-$C_{30}$ aryl, $C_2$-$C_{30}$ heteroaryl, $C_7$-$C_{30}$ arylalkyl, $C_3$-$C_{30}$ heteroarylalkyl,
the wave line represents a covalent bond to the imine nitrogen atom,
G is in each group (Ia) independently selected from a quarternary carbon atom and from a cyclopropenylidene structural moiety,
x is an integer equal to one or higher, and
the lone electron pair of the imine nitrogen atom and/or the pi-electrons of the imine double bond of at least one group B is conjugated with the conjugated system of delocalized electrons comprised in the structural moiety A,
with the proviso that two or more of the substituents $R^1$, $R^2$, $R^3$, $R^4$ may be connected to form a ring that may contain also unsaturation and, if any of the substituents $R^1$, $R^2$, $R^3$, $R^4$ comprises two or more carbon atoms, up to one third of the overall count of the carbon atoms in the substituent or in any ring formed by two connected substituents can be replaced with heteroatoms independently selected from O, S, N and B.

13. Organic electronic device according to claim 12, wherein x is an integer selected from 2, 3 and 4 and the lone electron pairs of the imine nitrogen atoms and/or the pi-electrons of the imine double bonds of at least two groups B are conjugated with the conjugated system of delocalized electrons comprised in the structural moiety A.

14. Organic electronic device according to claim 12, wherein A is a $C_3$-$C_{40}$ arene or $C_2$-$C_{40}$ heteroarene structural moiety that contains one conjugated system of delocalized electrons.

15. Organic electronic device according to claim 12, wherein A is a $C_6$-$C_{18}$ arene or $C_4$-$C_{18}$ heteroarene structural moiety and the lone electron pairs of the imine nitrogen atoms and/or the pi-electrons of the imine double bonds of all groups B are conjugated with the conjugated system of delocalized electrons comprised in the structural moiety A.

16. Organic electronic device according to claim 12, wherein the layer comprising the n-dopant is an electron transport layer or an electron injection layer.

17. Organic electronic device according to claim 12, wherein the layer comprising the n-dopant is an electron transport layer comprising an electron transport matrix and having a thickness of more than 50 nm, or a neat layer having a thickness less than 5 nm.

18. Organic electronic device according to claim 12, wherein the layer comprising the n-dopant is in direct contact to the anode or the cathode.

19. Organic electronic device according to claim 12, further comprising an electron transport layer, wherein the layer comprising the n-dopant is in direct contact to the electron transport layer.

20. Organic electronic device according to claim 12, further comprising a light absorbing unit, wherein the layer comprising the n-dopant is part of a pn-junction connecting the light absorbing unit to an additional light absorbing unit in a tandem device or in a multiple stacked device and/or a pn-junction connecting the cathode or the anode to the light absorbing unit.

* * * * *